United States Patent [19]

Harms et al.

[11] Patent Number: 4,946,458
[45] Date of Patent: Aug. 7, 1990

[54] PEDICLE SCREW

[76] Inventors: Jürgen Harms, Am Rüppurer Schloss 5, D-7500 Karlsruhe; Lutz Biedermann, Am Schäfersteig 8, D-7730 VS-Villingen, both of Fed. Rep. of Germany

[21] Appl. No.: 317,144

[22] Filed: Feb. 28, 1989

Related U.S. Application Data

[63] Continuation of Ser. No. 38,734, Apr. 15, 1987, abandoned.

[30] Foreign Application Priority Data

Apr. 25, 1986 [DE] Fed. Rep. of Germany ....... 3614101

[51] Int. Cl.$^5$ ................................. A61F 2/00
[52] U.S. Cl. .................................... 606/61; 606/72; 606/57; 623/17
[58] Field of Search ............... 128/69, 92 YF, 92 YE, 128/92 YM, 92 YV, 92 Z, 92 ZK, 92 ZW, 92 ZY, 92 ZZ; 403/55, 57, 84, 88, 90, 122, 141–143; 606/60, 61, 62, 65, 67, 72, 73, 57, 59

[56] References Cited

U.S. PATENT DOCUMENTS

| | | | |
|---|---|---|---|
| 958,052 | 5/1910 | Williams | 403/142 |
| 3,554,193 | 1/1971 | Konstantinou et al. | 128/92 YV |
| 3,997,138 | 12/1976 | Crock et al. | 128/92 YF |
| 4,127,119 | 11/1978 | Kronner | 128/927 |
| 4,135,505 | 1/1979 | Day | 128/92 Z |
| 4,274,401 | 6/1981 | Miskew | 128/69 |
| 4,456,004 | 6/1984 | Kenny | 128/92 ZW |
| 4,569,338 | 2/1986 | Edwards | 128/69 |
| 4,570,625 | 2/1986 | Harris et al. | 128/92 ZY |
| 4,611,582 | 9/1986 | Duff | 128/69 |
| 4,648,388 | 3/1987 | Steffee | 128/92 YF |
| 4,653,481 | 3/1987 | Howland et al. | 128/69 |
| 4,653,481 | 3/1987 | Howland et al. | 128/92 YM |

FOREIGN PATENT DOCUMENTS

| | | |
|---|---|---|
| 2649042 | 5/1978 | Fed. Rep. of Germany . |
| 3306657 | 9/1984 | Fed. Rep. of Germany . |
| 3504495 | 10/1985 | Fed. Rep. of Germany . |

Primary Examiner—Robert A. Hafer
Assistant Examiner—Lynda M. Cofsky
Attorney, Agent, or Firm—Donald Brown

[57] ABSTRACT

A pedicle screw (1) for use in the monosegmental or multisegmental stabilization of the spinal column comprises a thread and a receiver portion. In order to facilitate the mounting and to reduce the stress of the screw and the threaded rods for connection therewith, a threaded shaft part (2) and a receiver part (3) are mutually connected in an articulated manner.

5 Claims, 3 Drawing Sheets

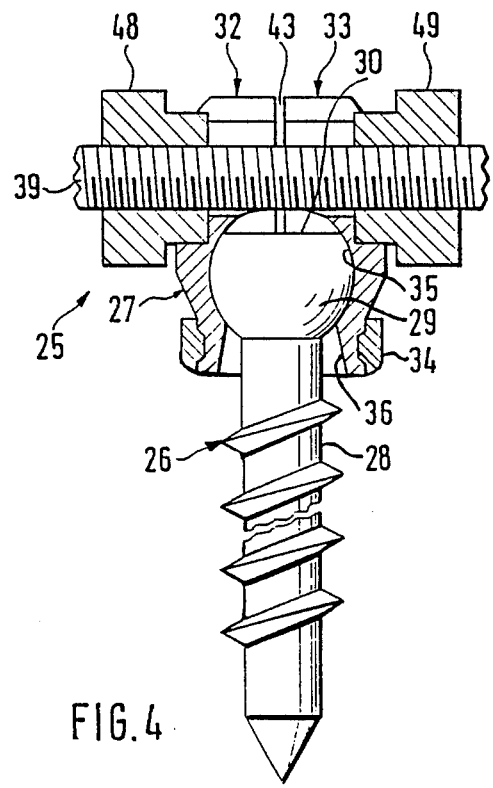
FIG. 11
FIG. 4
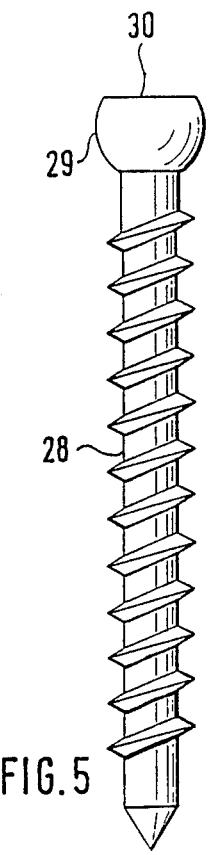
FIG. 5
FIG. 6

PEDICLE SCREW

This is a continuation of co-pending application Ser. No. 07/308,734 filed on Apr. 15, 1987 now abandoned.

BACKGROUND OF THE INVENTION

The invention relates to a pedicle screw having a threaded shaft part and a receiver part provided at the head side of the threaded shaft part and being adapted for receiving a bar.

Such screws are used in the monosegmental or multisegmental fixation of the spinal column. A predicle screw of this kind is known from the German patent specification No. 26 49 042. The screw comprises a threaded portion and a receiver portion rigidly connected thereto at the head end. Several pairs of such screws are screwed into the vertebrae on both sides of the spinal column in a respective distance from each other. The respective receiver portions comprise receiving slits. A respective threaded bar is passed thorugh these receiving slits of the right and left group of the screws. Thereafter the bar is fixed to the respective receiver portion by means of fastening screws. It is a drawback of this solution that it is difficult to rigidly screw these screws into the vertebrae and at the same time position the screws in two planes in exactly such a manner that the axes of the receiving slits in the receiver parts in the vertical columns are aligned such that the threaded rod may be passed through the receiving slits without distortion of the screws. Even the attempt to do this requires a lot of time which is very disadvantageous for an operation at the spinal column. Moreover such an exact alignment can hardly be achieved. As a result relevant shearing forces act upon the threaded rods which causes a possible break of the rods in use after the operation or a lack of fixation.

OBJECTS OF THE INVENTION

It is an object of the invention to provide an improved pedicle screw, in which the above mentioned drawbacks are avoided. It is a further object to provide a pedicle screw of the above mentioned kind which facilitates the mounting operation and at the same time reduces or avoids dangers in the later use.

SUMMARY OF THE INVENTION

According to the invention a pedicle screw stabilizing spinal segments comprises a threaded shaft part and a receiver part being provided at the head side and being adapted to receive a bar, the threaded shaft part and the receiver part being connected with each other in an articulated manner.

It is achieved in that manner that, to begin with, the screw may be screwed in regardless of the position of the receiver part and thereafter the receiver part may easily be brought into the position required for receiving the threaded bar. This results in an essential reduction of operation time and of the forces acting on the threaded bar.

BRIEF DESCRIPTION OF THE DRAWINGS

Further advantages, features and objects of the invention will stand out from the following description of exemplary embodiments with reference to the drawings. In the drawings

FIG. 4 is a lateral and partly sectional view of a second embodiment;

FIG. 5 shows a part of FIG. 4 on an enlarged scale;

FIG. 6 is a top view of the part shown in FIG. 5;

FIG. 11 shows a ring member of the embodiment shown in FIG. 4 on an enlarged scale.

Figure 1:
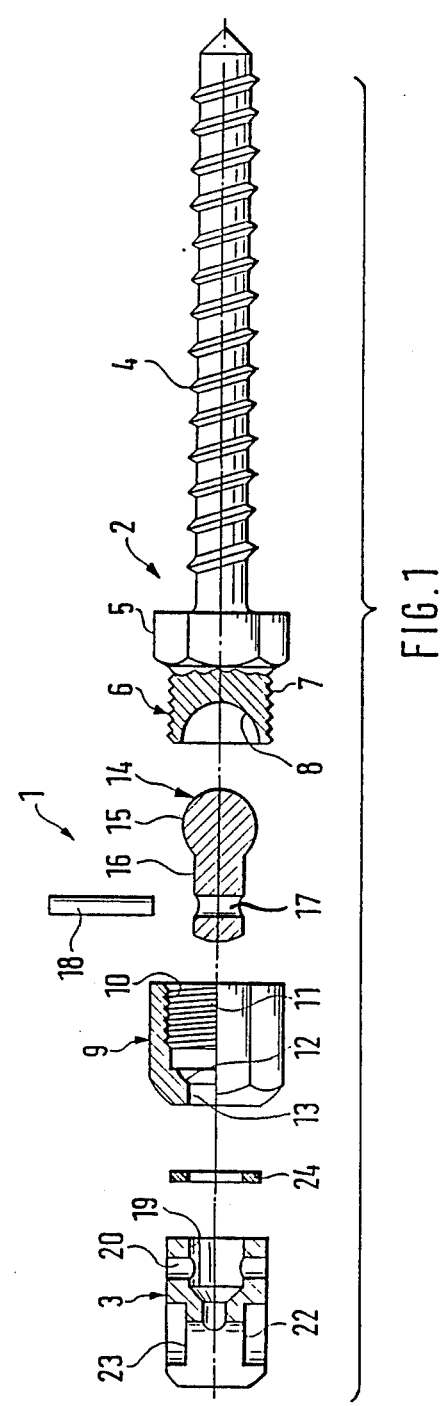
FIG. 1 shows a first embodiment of a pedicle screw in exploded, partly sectional and enlarged representation.
Figure 2:
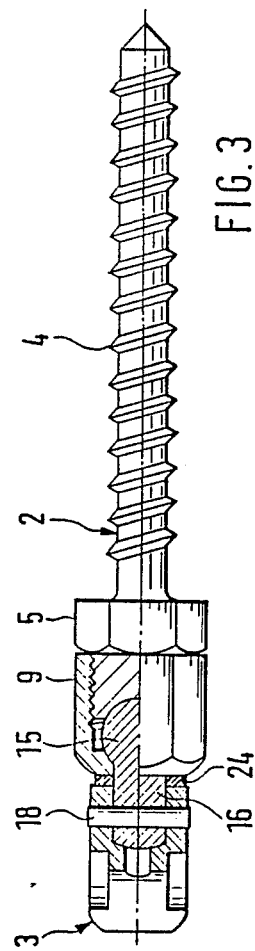
FIG. 2 shows the receiver part turned by 90° with respect to the position shown in FIG. 1.
Figure 3:
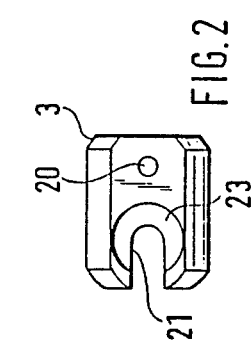
FIG. 3 is a combined representation of the screw shown in FIG. 1.
Figure 7:
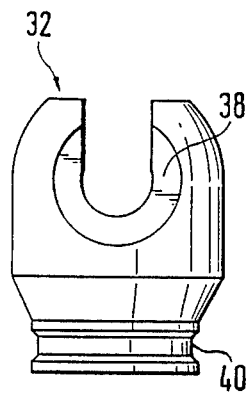
FIG. 7 shows a part of FIG. 4 on a changed scale.
Figure 8:
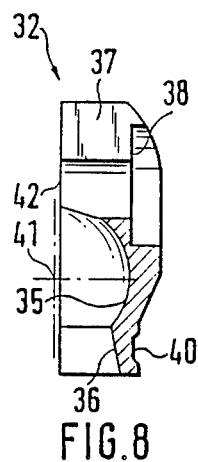
FIG. 8 is a partly sectional repesentation of the part shown in FIG. 7 turned by 90°.

In the first embodiment shown in the FIGS. 1 to 3 the pedicle screw 1 comprises a threaded shaft part 2 and a receiver part 3.

The threaded shaft part comprises a conventionally designed threaded portion 4 adapted to be screwed into the vertebrae. A hexagon head 5 is provided at the head end of the threaded portion. A projection 6 having an external thread 7 follows at the side opposite to the threaded portion. The projection 6 has a recess 8 in the form of a spherical segment provided at the size thereof which is opposite to the threaded portion. The threaded portion 4, the hexagon head 5, the projection 6 and the recess 8 are aligned coaxially with each other in the manner shown in FIG. 1.

A lock nut 9 is provided associated to the threaded shaft part. The lock nut is a hexagon screw which comprises a recess 11 having an internal thread 10 and being provided at the side thereof facing the threaded shaft part 2. The dimensions of the internal thread are selected such that the internal thread fits to the external thread 7. A portion 12 shaped as a spherical segment follows the bottom of the recess 11. The radius of the spherical segment substantially corresponds to the radius of the recess 8. The open side of the spherical segment shaped recess is opposite to the recess 8. A bore 13 follows the recess 12 at the side opposite to the projection 6. The recess 11 with the internal thread 10, the sphercial segment shaped recess 12 and the bore 13 are aligned coaxially with each other.

A connecting member 14 is provided which comprises a spherical segment shaped or spherical portion 15 and a cylindrical portion 16 following the spherical portion and forming a single unitary part therewith. A bore 17 adapted to receive a locking pin 18 is provided in the cylindrical portion in a direction perpendicular to the axis of the cylindrical portion. The radius of the portion 15 is closely equal to an only slightly smaller than the radius of the two recesses 8 and 12. The diameter of the cylindrical portion 16 is smaller than the diameter of the bore 13 such that the connecting member having the cylindrical portion at the leading side may be put through the recess 11 and the bore 13 and projects outwardly from the bore 13. The threads 7 and 10 are selected as a function of the diameters of the recesses 8 and 12 and of the spherical segment shaped portion 15 such that it just allows a movement of the cylindrical portion within a cone around the center of the spherical segment shaped portion 15 in one position when the connecting member is mounted and the lock nut 9 is screwed on. The extent of the movement is predetermined by the difference of the size of the bore 13 and the outer diameter of the cylindrical portion 16.

The lock nut 9 may be tightened such that a substantially stiff connection results between the connecting member 14 and the threaded portion 4.

The receiver part 3 is designed in a cylindrical manner with the axis of symmetry thereof being aligned with the axis of symmetry of the threaded shaft part 2. A coaxially extending inner bore 19 is provided at the side facing the threaded shaft part. The diameter of the inner bore 19 is selected such that the cylindrical portion 16 just fits therein. A cross-bore 20 is provided perpendicularly to the direction of the inner bore 19 and has the dimension thereof selected such that the locking pin may snugly fit therein. The depth of the inner bore 19 and the location of the bore 20 are selected such that the cylindrical portion 16 having the lock nut rigidly mounted thereto may be inserted into the inner bore 19 in the manner shown in FIG. 1 and may be locked by means of the locking pin 18. The receiver part has a receiving slit 21 provided at the end opposite to the bore 19. The receiving slit 21 extends perpendicularly to the axis of symmetry of the receiver part and has recesses 22 and 23 provided at both outsides thereof. The width of the receiving slit 21 is selected such that the threaded rods to be fitted therein may loosely be passed therethrough. A damping washer 24 made of a material with damping properties such as silicon is provided between the lock nut 9 and the receiver part 3.

According to one embodiment the surfaces of the recesses 8 and 12 and/or of the spherical segment shaped portion 15 are polished or coated with an anti-friction means such as Teflon, such that a slight dampened movement of the cylindrical member is possible even in case that the lock nut 9 is tightened. According to a further embodiment the surfaces are made uneven such that the ball virtually jams in the mounted position with tightened lock nut 9 and a substantially stiff connection between the connecting member 14 and the threaded portion 4 is obtained.

The lock nuts 9 are removed or loosened, respectively, for inserting the pedicle screws into the respective vertebrae. After the insertion the direction of the receiver part 3 is aligned such that the threaded rods may be aligned without any action of shearing forces. Thereupon the threaded rods are fixed with fastening screws positioned in the respective recesses 22, 23. Thereafter the respective lock nut 9 is either, as desired, tightened such that the connecting member 14 may nearly or not at all move any more and hence a substantially stiff or rigid connection between the receiver part 3 and the threaded shaft part 2 is obtained, or it is tightened only to such an extent that it allows a desired dampened movement between both parts.

In the embodiment shown in the FIGS. 4 to 11 the transpedicle screw 25 comprises a threaded shaft part 26 and a receiver part 27.

The threaded shaft part 26 comprises a threaded portion 28 adapted to be screwed into the vertebrae. A spherical segment shaped head 29 is provided at the head end of the threaded portion. The head 29 has a plane surface 30 extending normally to the axis of the threaded portion 28 and being provided at the side of the head opposite to the threaded portion. The surface 30 is formed by cutting off a section of the sphere. The cut-off portion corresponds to about half a radius of the spherical body.

A hexagon bore 31 is provided coaxially to the threaded portion 28, as may be seen from FIG. 6. The hexagon bore 31 may be engaged by a hexagon socket screw key for screwing the threaded shaft part 26 into the vertebrae. Certainly other types than the hexagon bore may be provided for engaging by means of a screw driver.

The receiver part 27 comprises two head halves 32, 33 as well as a retaining ring 34 holding the head halves together.

Each head half has a spherical segment shaped portion 35 at the inner side thereof facing the other head half. The inner radius of the ball corresponds to the radius of the head 29. The spherical segment shaped portion is followed by a collar portion 36 which has the form of a segment of a truncated cone and is designed to divert outwardly from the spherical segment shaped portion. The axis of the collar portion passes through the center of the spherical segment shaped portion 35. A receiving slit 37, FIGS. 8, 9 and 10, extends perpendicularly to the axis of symmetry of the collar portion and the spherical segment shaped portion at the side of the spherical segment shaped portion 35 which is opposite to the collar portion. The receiving slit 37 hs a recess 38 provided at the outside thereof which is opposite to the other head half. The width of the receiving slit is selected such that a threaded rod 39 to be fitted therein may be loosely passed therethrough, as may be seen in FIG. 4.

The head half has a groove shaped recess 40 provided in the region of the collar portion 36 and extending perpendicularly to the axis of symmetry of the collar portion and the spherical segment shaped portion.

The two head halves 32, 33 are formed in identical manner. Their dimensions are selected such that the center 41 of the spherical segment shaped portion 35 lies outside by a fraction of a millimeter of the respective separating plane 42 which is opposite to the respective second head half, so that a gap 43 is obtained between both halves when the two head halves 32, 33 are assembled parallel to each other around the head.

The retaining ring 34 has an inner surface 44 which practically represents the negative or counter mould of the outer surface of the collar portion 36. In particular the inner surface 44 comprises a projecting enlargement 45, which fits into the groove shaped recess 40, and respective adjacent lateral edge portions 46, 47. The inner diameter of the retaining ring 34, in particular that of the enlargement 45 and the edge portions 46, 47 is selected such that the tension exerted by the ring 34 onto both head halves 32, 33 in a state where both head halves are mounted on the head 29 without the threaded rod 39 being inserted, as shown in FIG. 4, is such that they may freely pivot around the longitudinal axis of the threaded shaft portion 36 within an angle which is determined by the amount of taper of the collar portion 36, and that they are connected with the head and hence with the threaded shaft portion 26 in a rigid manner sufficient for insertion of the threaded bar 39 such that both head halves are closer together in the region surrounded by the ring than in the opposite region comprising the receiving slit.

Figure 9:
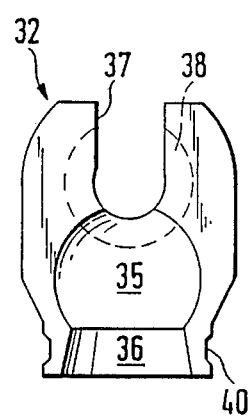
FIG. 9 is a back view of the part shown in FIG. 7.
Figure 10:
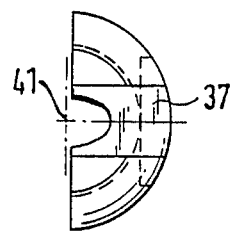
FIG. 10 is a top view of the part shown in FIG. 8.

As may be in particular seen from the FIGS. 4 and 9, the depth of the receiving slit 37 is selected such that the slit ends, in the assembled state shown in FIG. 4 in a distance above the surface 30 in order to avoid a restriction of the free movability of the receiver part 27 around the longitudinal axis of the threaded shaft part 36.

For mounting the pedicle screw according to the embodiment ment shown in the FIGS. 4 to 11, the transpedicle screw is at first screwed into the respective vertebrae by engagement of a hexagon socket screw key into the hexagon bore through the receiving slits. After the screwing-in the receiver part 27 with both head halves 32, 33 held togehter by the retaining ring 34 are directionally aligned such that the threaded rods 39 may be inserted into the receiving slits 37 without any action of shearing forces. Thereupon the threaded rods are fixed by means of respective fastening screws 48, 49 sitting in the recesses 38. The fastening screws may as desired either be tightened such that the receiver part 37 cannot pivot around the head 29 and hence a substantially stiff connection between the receiving part 27 and the threaded shaft part 26 is obtained, or the screws are only tightened such that a desired dampened movement between both parts is still possible.

By using both of the above described embodiments of the pedicle screw an unlimited free movement around the axis of symmetry and a preadjustable movement which is preferable in an angle region from 10° to 30° in horizontal and vertical direction is obtained. In the last described embodiment it is additionally achieved that the overall length of the pedicle screw is particularly short.

In the embodiment shown in FIG. 4 the retaining ring 34 is rounded on the side thereof facing the threaded portion 28 by a radius having a center on the side opposite to the threaded portion 28. The lower side of the hexagon head 5 facing the threaded portion 4 may be rounded in a corresponding manner. It is a result of this radius that the surfaces facing the respective vertebrae cannot cause any injuries at those portions.

Although the invention has been described with reference to specific example embodiments, it is to be understood that it is intended to cover all modifications and equivalents within the scope of the appended claims.

What is claimed is:

1. A pedicle screw for stabilizing spinal segments comprising a shaft embodying a thread shank, a partially spherical-shaped head at one end of the threaded shaft, a receiver part embodying two halves for receiving the head of the shaft and a ring disposed about said halves for holding the halves in embracing engagement with said head.

2. A pedicle screw according to claim 1 wherein said receiver halves embody diametrically-opposed, concave, spherical portions engaged with said head.

3. A pedicle screw according to claim 2 wherein said receiver halves are so dimensioned that there is a gap between the halves.

4. A pedicle screw according to claim 1 wherein said head comprises means for engagement with a screw driver.

5. A pedicle screw according to claim 1 wherein said receiver halves contain circumferentially thereof grooves and said ring embodies an internal circumferential projection engaged within said grooves.

* * * * *